United States Patent [19]

Utz

[11] Patent Number: Plant 5,999

[45] Date of Patent: Sep. 1, 1987

[54] ROSE PLANT NAMED SAVAPEG

[75] Inventor: Peggy L. Utz, New Albany, Ind.

[73] Assignee: Nor'East Miniature Roses, Inc., Rowley, Mass.

[21] Appl. No.: 783,115

[22] Filed: Oct. 2, 1985

[51] Int. Cl.[4] ..... A01H 5/00

[52] U.S. Cl. ..... Plt./9

[58] Field of Search ..... Plt./9

*Primary Examiner*—Robert E. Bagwill

*Attorney, Agent, or Firm*—Vincent G. Gioia

[57] ABSTRACT

A new miniature rose variety of varying pale rose flower coloring.

1 Drawing Figure

1

The present invention relates to a new and distinct variety of rose plant of the miniature rose class, which is a color mutation (sport) of the miniature rose known as "Starina" (U.S. Plant Pat. No. 2,646) that I discovered in my glass house. The varietal denomination of this new variety is "Savapeg".

Among the novel characteristics possessed by this new variety which distinguish it from the cultivar from which it sported and all other varieties of which I am aware are its flowers of good exhibition form with varying pale rose tonality from Empire rose to Claret rose that maintain their color and form through development and aging. Asexual reproduction by budding of the new variety as performed in Essex County, Mass., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "49B" is plate 49B of The Royal Horticultural Society Colour Chart.

Parentage: Mutation of the miniature rose known as "Starina".

Class: Miniature.

The following observations are made of specimens grown outdoors in Essex County, Mass., during the month of May.

FLOWER

Blooming habit: Recurrent.

A. Bud:
- (1) *Size.*—Medium.
- (2) *Form.*—Ovate, pointed.
- (3) *Color.*—When sepals first divide — bud color appears Venetian pink, near 49B; petal undersurface and top surface appear of similar coloring but petal undersurface shows yellow tonality towards point of petal attachment.
- (4) *Sepals.*—Simple, longer than bud, smooth.

2

- (5) *Peduncle.*—Length — about ¾ to 1". Aspect — straight. Strength — erect. Color — near 144C.

B. Bloom:
- (1) *Size.*—Average size when fully expanded — about 1¼ to 1½ inches.
- (2) *Borne.*—Singly and small sprays.
- (3) *Form.*—High centered at first, with center holding through ¾ open stage, petals reflex to point and maintain good exhibition form as flower opens.
- (4) *Petalage.*—Number of petals under normal conditions — about 25.
- (5) *Color.*—After sepals fall, flowers open in good exhibition form with color ranging from Empire rose, 48D, to Claret rose, 50D. As flowers open further, outer petals lighten to near 65B to 65C. Veining is visible in most petals, especially outer petals. Petal top and under surfaces appear of similar tonality. Where petals bunch, as in flower centers, tonality appears darker.

C. Petals:
- (1) *Texture.*—Thick.
- (2) *Appearance.*—Inside — velvety, outside — satiny.
- (3) *Form.*—Broad, fan shaped with pronounced apex on some petals.
- (4) *Arrangement.*—Regularly arranged, imbricated.
- (5) *Petaloids in center.*—Few to none.
- (6) *Persistence.*—Drop off cleanly.
- (7) *Fragrance.*—Slight.
- (8) *Lasting quality.*—Very long on plant and as cut flower.

REPRODUCTIVE ORGANS

A. Stamens, filaments and anthers:
- (1) *Arrangement.*—Regularly arranged around styles.
- (2) *Color.*—near 17C.

B. Pollen:
- *Color.*—near 17A.

C. Styles: Even length, short.

D. Stigmas:
- *Color.*—Near 186B.

E. Hips: None observed.

PLANT

A. Form: Spreading, upright.

B. Growth: Very vigorous.
- *Height attained.*—About 16 to 18 inches.

C. Foliage: Compound 5 to 7 leaflets.

(1) *Size.*—Medium.
(2) *Quantity.*—Abundant.
(3) *Color.*—New foliage: Upper side — near to 138A. Under side — near to 139C. Old foliage: Upper side — near 139A. Under side — near 139C.
(4) *Shape.*—Oval, pointed.
(5) *Texture.*—Upper side is glossy and under side is matte.
(6) *Edge.*—Serrated.
(7) *Serration.*—Serrate.
(8) *Leaf stem.*—Color — near 137C. Under side — near 137D.
(9) *Stipules.*—Medium, slightly bearded.
(10) *Resistance to disease.*—Blackspot — average. Mildew — average. Rust — average.

D. Wood:
(1) *New wood.*—Color — near 143A. Bark — smooth.

(2) *Old wood.*—Color — near 146C. Bark — smooth.

E. Thorns:
(1) *Thorns.*—Quantity (main stalk) — ordinary. On laterals from stalk — few. Form — straight, pointed. Length — small. Color — near 186B. Position — irregular.
(2) *Prickles.*—Few.

F. Winter hardiness: Requires ordinary protection in extreme climates.

I claim:

1. A new and distinct variety of rose plant of the miniature rose class, substantially as shown and described, which is a sport of the miniature rose "Starina" producing exhibition form flowers of varying pale rose tonality that hold color well through development and aging.

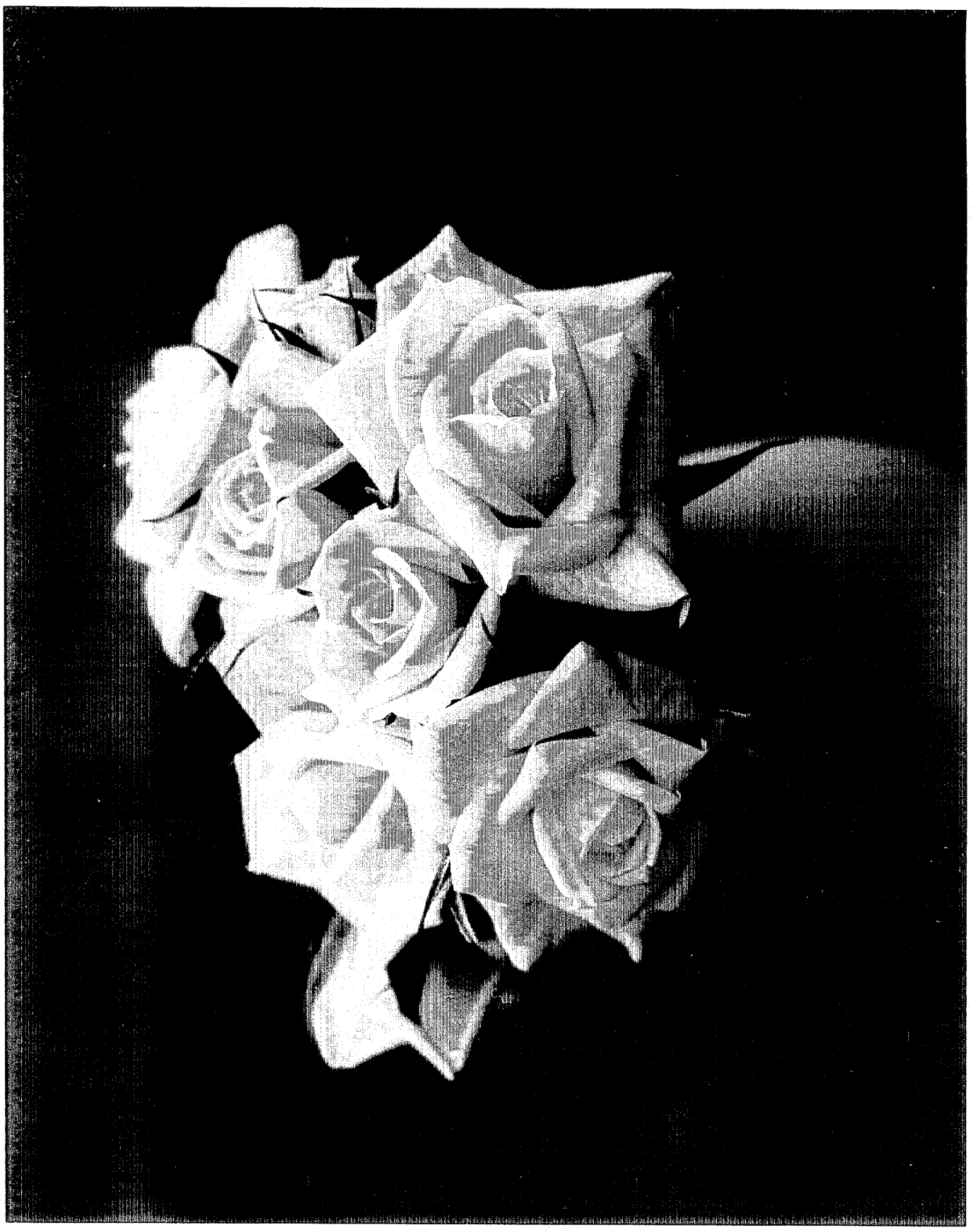

* * * * *